United States Patent [19]

Bonjouklian et al.

[11] Patent Number: 4,647,685
[45] Date of Patent: Mar. 3, 1987

[54] 2-ALKOXY-1-((2-TRIALKYLAMINOETHOXY)PHOSPHINYLOXY)-ALKENES AND ALKYNES, HYDROXY INNER SALTS

[75] Inventors: Rosanne Bonjouklian; Michael L. Phillips, both of Indianapolis, Ind.

[73] Assignee: Eli Lilly and Company, Indianapolis, Ind.

[21] Appl. No.: 727,304

[22] Filed: Apr. 25, 1985

[51] Int. Cl.$^4$ ................................ C07F 9/11
[52] U.S. Cl. ................................ 558/169; 568/678
[58] Field of Search .................. 260/925; 558/169

[56] References Cited

U.S. PATENT DOCUMENTS

| 4,426,330 | 1/1984 | Sears | 260/403 |
| 4,426,525 | 1/1984 | Hozumi et al. | 546/22 |
| 4,542,219 | 9/1985 | Hozumi et al. | 260/925 |
| 4,562,179 | 12/1985 | Teraji et al. | 260/925 |

FOREIGN PATENT DOCUMENTS 92190 10/1983 European Pat. Off.

OTHER PUBLICATIONS

Derwent Abstract 98882 E/46—Ono Pharmaceutical, 10/12/82.
Derwent Abstract 18140 K/08—Takeda Chemical Ind KK, 11/4/82.
Derwent Abstract 17735 K/08 Fujisawa Pharm KK Ltd., 2/16/83.
Derwent Abstract 12632 K/06—Fujisawa Pharm KK Ltd., 1/26/83.
Derwent Abstract 10077 K/05—Boehringer Mannheim GmbH, 7/18/81.
Modolell et al., Can. Res., 39, 4681, (1979).
Chang et al., Biochem. & Biophys. Res. Comm., 54, 648 (1973).
Wykle et al., Febs. Letters, 141, 29 (1982).
Tidwell et al., Blood, 57, 794 (1981).
Demopoulos et al., J.B.C., 254 9355 (1979).
Wissner et al., J. Med. Chem., 27, 1174 (1984).

Primary Examiner—Anton H. Sutto
Attorney, Agent, or Firm—Charles W. Ashbrook; Leroy Whitaker

[57] ABSTRACT

2-Alkoxy $C_{12-26}$ straight chain ethylenic or acetylenic hydrocarbyl hydroxy phosphonyl cholenic, useful as platelet aggregation modifiers and antitumor agents.

9 Claims, No Drawings

2-ALKOXY-1-((2-TRIALKYLAMINOETHOXY)-PHOSPHINYLOXY)-ALKENES AND ALKYNES, HYDROXY INNER SALTS

BACKGROUND OF THE INVENTION

The term "phospholipid" is generic to several different types of compounds originating in the mammalian cell and containing long chain fatty acid esters of glycerol attached to various polar groupings. Lecithin, a phosphatidic acid ester of choline, is one of a group of phospholipids of structure I below

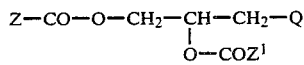

wherein Z and $Z^1$ are long, straight-chain alkyl or alkenyl radicals and

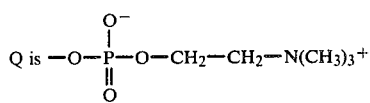

A related substance is platelet-activating factor (PAF)—see Demopoulos et al, J. Biol. Chem., 254, 9355 (1979)—having structure Ia below

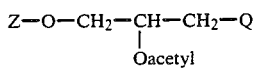

in which there is an ether linkage on C-1, a short chain fatty acid ester (acetate) at C-2, Z is $C_{16}$-$C_{18}$ alkyl and Q has its previous meaning. A number of analogues of PAF have been synthesized. Among these are compounds of structure Ib below described in FEBS Letters, 14 29 (1982), see also Modell et al, Can. Res., 39, 4681 (1979) which describes the activity of such compounds in selectively destroying Meth A sarcoma cells.

where $Z^2$ is alkyl or H; and Q has its previous meaning.

Other substitutions such as chloro for the C-2 acyloxy of PAF are known.

Diethers of structure Ic are also known—

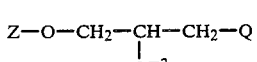

See U.S. Pat. No. 4,426,525 where Z is tridecyl or tetradecyl.

The compound wherein Z is $C_{18}H_{37}$ and $Z^2$ is methyl inhibits the proliferation of leukemic cells according to Tidwell et al., Blood, 57, 794 (1981)—see also Derwent Abstract 17735 K/08 and Derwent Abstract 98882 E/46.

Compounds lacking the C-1 oxygen have also been prepared; ie., compounds of the structure

where Z is $C_{13}$—$H_{27}$(CAS 51814-79-0); Z is $C_{12}H_{25}$ and the C-2 hydroxyl is esterified (CAS 54646-41-2) and Q has its previous meaning—see also Derwent Abstract 12632 K/06 (an ortho ester) and Chang, et al. *Biochem. and Biophys. Res. Comm*; 54, 648 (1973) particularly Scheme 1, page 652, and related disclosure.

Ethers of compounds according to Id have recently been disclosed in EPO application 92,190 published Oct. 26, 1983 based on G.B. 82-11284 filed Apr. 19, 1982, as represented by formula Ie

where Z is alkyl, alkoxy or alkanoylamino and $Z^1$ is lower alkyl, lower alkanesulfonyl or arenesulfonyl; dl-2-methoxy-1-[(2-trimethylaminoethoxy)phosphinyloxy]-octadecane, hydroxy inner salt, is specifically disclosed. The compounds are alleged to inhibit the growth of Meth A sarcoma transplanted in mice.

Compounds according to Ie in which Z contains one or more unsaturations (double or triple bonds) are not known, nor will the procedure of EPO 92190 furnish such compounds.

SUMMARY OF THE INVENTION

This invention provides 2-alkyloxy-1-[(2-tri($C_{1-2}$ alkyl)aminoethoxy)phosphinyloxy]$C_{12-26}$ alkenes, alkadienes, alkynes etc, hydroxy inner salts, of the formula

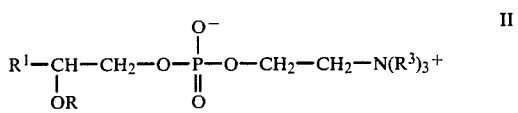

wherein R is $C_{1-6}$ alkyl, preferably $C_{1-3}$ straight chain alkyl, $R^1$ is straight-chain $C_{10-24}$ alkenyl or alkynyl; ie. a hydrocarbyl radical containing at least one ethylenic or acetylenic unsaturation; and each $R^3$ is individually methyl or ethyl. R in the above formula includes methyl, ethyl, n-propyl, isobutyl, n-amyl, isoamyl, n-hexyl,sec-butyl, isopropyl and the like, and $R^1$ includes the alkenyl groups, undec-trans 4-enyl, undec-trans 2-enyl, undec-11-enyl, tridec-9-enyl, tetradec-6-enyl, pentadec-trans 3-enyl, pentadec-6-enyl, pentadec-cis 9-enyl, heptadec-cis 9-enyl, heptadec-cis-6-enyl, heptadec-11-enyl, heptadec-cis 12-enyl, and heptadec-cis 12-enyl; the alkynyl group, heptadec-6-ynyl(tariryl) and heptadec-9-ynyl; and the polyunsaturated groups, pentadec-2,4,8,10-tetraenyl, heptadec-cis 5,11-dienyl, heptadec-9,12-dienyl, heptadec-trans 10,trans 12-dienyl, heptadec-cis 7,cis 11-dienyl, heptadec-trans 11-en-9-ynyl, heptadec-cis 9,cis 12, cis 15-trienyl, heptadec-6,9,12-trienyl, heptadec-9,11,13-trienyl, heptadec-trans 13-ene-9,11-diynyl, heptadec-trans 11, trans 13-dien-9-ynyl, heptadec-8,10,12-trienyl, heptadec-5,11,14-trienyl, heptadec- trans 5,cis 9,cis 12-trienyl, heptadec-17-ene-9,11-diynyl, heptadec-9,11,13,15-tetraenyl, heptadec-cis 6,-cis 9,cis 12,cis 15-tetraenyl; and the like groups.

An alternate and preferred naming system is the E-Z system approved by IUPAC using the CIP (Cain-Ingold-Prelog rules). Certain of the above radicals (those in which cis or trans is specified) are named by this system as follows: (E)-4-indecenyl, (E)-2-undecenyl, (E)-3-pentadecenyl, (Z)-9-pentadecenyl, (Z)-9-heptadecenyl, (Z)-6-heptadecenyl, (Z)-12-heptadecenyl, (Z,Z)-5,11-heptadecadienyl, (E,E)-10,12-heptadecadienyl, (Z,Z)-7,11-heptadecadienyl, (E)-heptadec-11-en-9-ynyl, (Z,Z,Z)-9,12-15-heptadecatrienyl, (E)-heptadec-13-ene-9,11-diynyl, (E,E)-heptadeca-11,13-dien-9-ynyl, (E,Z,Z)-5,9,12-heptadecatrienzl, and (Z,Z,Z,Z)-6,9,12,15-heptadecatetraenyl.

A preferred group of compounds of this invention are those according to II in which $R^1$ is straight-chain $C_{12-22}$alkenyl or alkynyl. Other preferred groups are constituted of those compounds in which R is methyl or ethyl or those in which $R^3$ is methyl.

The first major step in the synthesis of compounds according to II above is the provision of a key intermediate 1-2-diol of the structure $R^1CHOHCH_2OH$.    III These diols have a center of asymmetry at C-2 and thus occur as racemic mixtures [a(d,l) or (±) pair]. These racemic diols can be resolved by methods available in the art such as by protecting the primary alcohol group by formation of a trityl ether thereon and then reacting the unprotected secondary alcohol group with an optically-active acid to form two diastereomeric esters. These diastereomers are not mirror images and thus can be separated mechanically; ie., by fractional crystallization or chromatography.

Compounds according to III above wherein $R^1$ has its previous meaning are produced by the reaction of an aldehyde with t-butoxymethyl potassium in the presence of LiBr, the Corey-Eckrich Reagent—see *Tetrahedron Letters*, 24, 3165 (1983). The product of this reaction, a 1-butoxy-2-hydroxyalkene or alkyne, is then etherified to yield a 2-alkoxy derivative (IV)

$R^1$—CHOR—CH$_2$O—t-Bu    IV

Removal of the t-butyl group with ferric chloride/acetic anhydride treatment followed by hydrolysis of any acetate formed with aqueous alkali, yields the desired 2-alkoxy-1-hydroxy derivative $R^1$—CHOR—CH$_2$OH    V The preparation of intermediates according to V is set forth in Reaction Scheme 1.

REACTION SCHEME 1

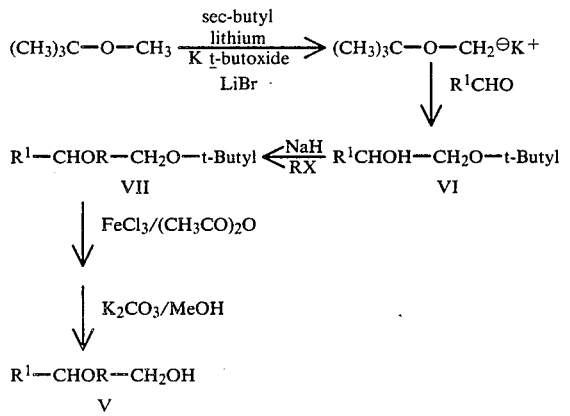

wherein R and $R^1$ have their previous meaning and X is a leaving group; ie, I, Br, Cl, p-tosyl and the like.

The aldehydes, $R^1$CHO, used as starting materials in Reaction Scheme I can be prepared from the corresponding acids or primary alcohols—See Rodd—The Chemistry of Carbon Compounds-Vol 1 (Elsevier NY 1965). The synthetic procedure for many novel unsaturated acids can also be found in the recent literature relating to leukotrienes and SRS-A—see Patent Office class 548/237 and related classes.

Once the key intermediate ether alcohol V ($R^1$—CHOR—CH$_2$OH), has been prepared (which compound can be either racemic or optically active), it can be converted to a compound represented by II above according to the following procedure which is based upon that found in Lipids, 14, 88 (1978):

Reaction Scheme 2

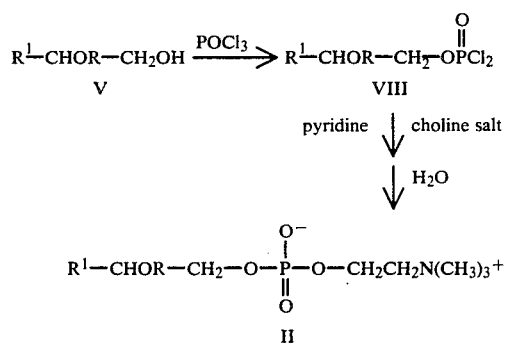

wherein R, $R^3$ and $R^1$ have their previous meanings, choline tosylate is the preferred choline salt.

An alternative scheme for preparing the compounds of this invention starting with the intermediate V (from Reaction Scheme 1) is set forth in Reaction Scheme 3 below:

REACTION SCHEME 3

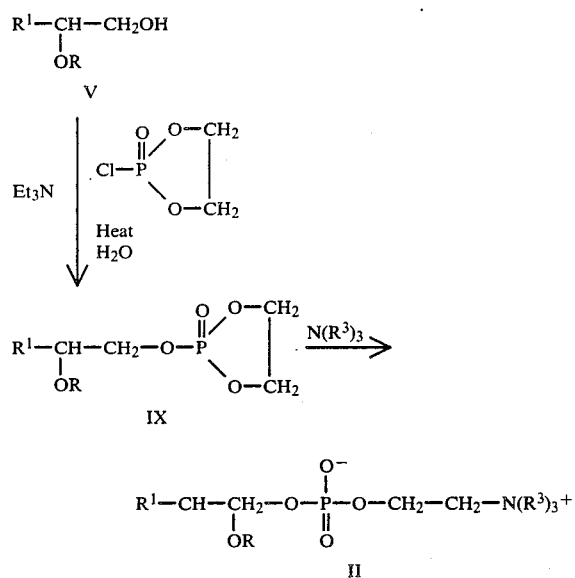

wherein R, $R^1$ and $R^3$ have their previous meaning. In the above reaction scheme, the primary alcohol is reacted with 2-chloro-1,3,2-dioxaphospholane-2-oxide

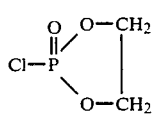

in a neutral, non-reacting solvent (ether, THF, THP) in the presence of an organic base (triethylamine, pyridine, quinoline) at room temperature or below under a $N_2$ atmosphere, following the procedure of Bull. Soc. Chim., 667, (1974). The product of the reaction is the cyclic phosphate (IX). Reaction of this cyclic phosphate with a trialkylamine $N(R^3)_3$ at elevated temperature (about 60° C.) in a non-reacting solvent, under pressure if necessary, yields a compound according to structure II. In the reaction with the trialkylamine, a useful solvent is acetonitrile. A sealed tube is usually employed.

Alternatively, V can be reacted with

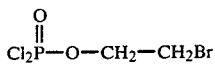

as set forth in Reaction Scheme 4 below.

REACTION SCHEME 4

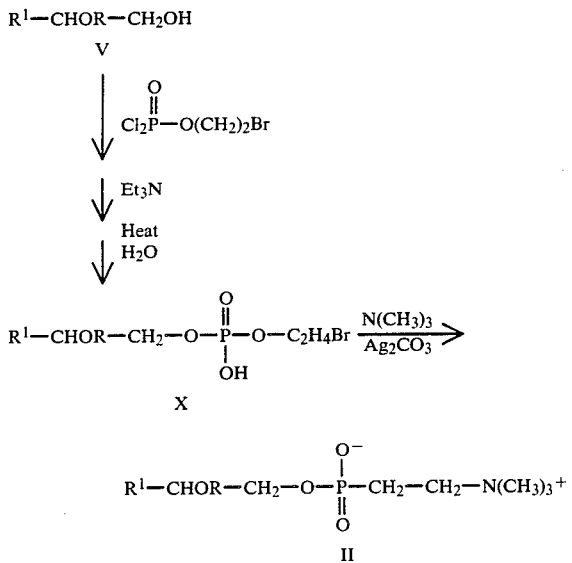

wherein R, and $R^1$ have their previous meaning.

Since choline is a trimethylammonium compound, Reaction Schemes 2 and 4 illustrate the preparation of compounds in which all $R^3$'s are methyl. If it is desired to prepare compounds in which at least one $R^3$ is other than methyl, intermediates of the structure

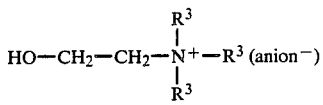

are used wherein each $R^3$ is methyl or ethyl, but one $R^3$ is other than methyl.

This invention is further illustrated by the following specific examples.

EXAMPLE 1

Preparation of (Z,Z)-(±)-2-Ethoxy-1-[(2-trimethylaminoethoxy)phosphinyloxy]-10,13 nonadecadiene, hydroxy inner salt A suspension of 28.3 g of powdered potassium t-butoxide in 400 ml of anhydrous t-butyl methyl ether was prepared at about −78° C. 180 ml of a 1.4M solution of sec-butyl lithium in cyclohexane was injected under the surface of the suspension over a 10 minute period. The resulting orange mixture was stirred for about 2 hours at which time 252 ml of a 2M solution of dry anhydrous lithium bromide in THF was added. The reaction mixture was allowed to warm to about −10° C. with stirring over a period of about 60 minutes. It was then cooled again to about −78° C. and 15.9 g of linoleyl aldehyde added. After about 15 minutes, the reaction mixture was quenched by the addition of about 50 ml of 10% aqueous ammonium chloride (pH=8). This mixture was diluted with ether and water and the organic layer separated. The organic layer was washed with brine and then dried. The volatile constituents were removed in vacuo, and the residue chromatographed over silica using cyclohexane with increasing quantities of ether (0–16%) as the eluant. Fractions containing (Z,Z)-(±)-1-(t-butoxy)-10,13-nonadecadiene-2-ol formed in the above reaction were collected; yield=11.8 g, (56%). The compound had the following physical properties: $R_f$=0.26 (5:1 cyclohexane/ether);

NMR (CDCl$_3$): δ at 2.05 (m, 4, 2CH$_2$CH$_2$CH=CH), 2.45 (d, 1, OH), 2.8 (m, 2, CH=CHCH$_2$CH=CH), 3.0–3.5 (m, 2, OCH$_2$), 3.7 (m, 1, OCH), 5.4 (m, 4, 2 CH=CH). Mass spectrum: peaks at 353, 338, 296.

A solution containing 5.9 g of the above alcohol in 67 ml of anhydrous THF was added to a 60% dispersion of sodium hydride in mineral oil (1.7 g). This suspension was heated at reflux temperature for about 1 hour at which time 6.7 ml of ethyl iodide were added by injection beneath the surface of the solution. The mixture was reheated to reflux temperature for another 1.5 hours, cooled and then quenched with water. Water and chloroform were added to the reaction mixture and the organic layer was separated. The organic layer was washed with brine and dried. Removal of the volatile constituents in vacuo yielded a residue comprising (Z,Z)-(±)-1-t-butoxy-2-ethoxy-10,13-nonadecadiene formed in the above reaction. This residue was suspended in 83.7 ml of acetic anhydride and the suspension cooled to about 0° C. 271 mg of anhydrous ferric chloride were added every 30 minutes until the reaction was seen to be proceeding as evidenced by TLC (5:1 hexane/ether). After for an additional 2 hours, the reaction mixture was extracted thrice with equal volumes of the hexane. The hexane extracts were combined, and the combined extracts washed with water and saturated aqueous sodium bicarbonate. The combined extracts were dried, and the volatile constituents were removed in vacuo. The residue was dissolved in methylene dichloride (41.8 ml) and this solution diluted with 83.7 ml of methanol. 2.54 g of solid potassium carbonate were added. After about 1.5 hours, methylene dichloride and water were also added. The organic layer was separated, the separated layer was washed with water and with brine and then dried. Removal of the volatile constituents in vacuo yielded a residue which was chromatographed over silica using cyclohexane containing increasing amounts of ethyl acetate (0–20%) as the eluant. Fractions containing (Z,Z)-(±)-2-ethoxy-10,13-nonadecadien-1-ol formed in the above reaction were collected. Removal of the solvent yielded 3.92 g of the desired material having the following physical characteristics. $R_f$=0.3 (2:1 cyclohexane/ether);

NMR (CDCl$_3$): δ at 2.0 (m, 5, 2CH$_2$CH$_2$CH=CH and 1H) 2.75 (m, 2, CH=CHCH$_2$CH=CH), 5.3 (m, 4, 2CH=CH); mass spectrum: peaks at 324, 293.

To a solution of POCl$_3$ (1.69 ml) in 12 ml of THF was added dropwise a solution of (Z,Z)-($\pm$)-2-ethoxy-10,13-nonadecadien-1-ol (3.92 g) and triethylamine (3.37 ml) in 60 ml of THF. After 35 minutes, the resulting suspension was quickly filtered, the solvent evaporated from the filtrate and the residue redissolved in a mixture of pyridine (7.54 ml) and chloroform (12.6 ml). Choline tosylate (7.33 g) was then added, and after 4.5 hours, 2.4 ml of water was introduced. After an additional 30 minutes, the reaction mixture was diluted with a double volume of a 3:2:1 chloroform/water/methanol. The organic phase was separated, and the separated phase washed with saturated aqueous sodium bicarbonate, dried and concentrated. The concentrate was then chromatographed on a silica column, eluting first with chloroform, and then a CHCl$_3$/MeOH gradient. The desired product (Z,Z)-($\pm$)-2-ethoxy-1-[(2-trimethylaminoethoxy)phosphinyloxy]-10,13-nonadecadiene, hydroxy inner salt, (1.80 g) was isolated having the following characteristics:

$R_f$=0.2 (10:5:1 chloroform/methanol/NH$_4$OH);

NMR (CDCl$_3$) $\delta$ at 2.0 (m , 4, 2, CH$_2$CH$_2$CH=CH) 2.75 (m, 2), 3.35 (s, 9, N(CH$_3$)$_3$), 4.3, (m, 2), 5.3 (m, 4, 2CH=CH); Mass spectrum peaks at 490, 184. Molecular Weight Calc'd. for C$_{26}$H$_{53}$NO$_5$P; 490.3662; Found; 490.3660.

EXAMPLE 2

Preparation of (Z)-($\pm$)-2-Ethoxy-1-[(2-trimethylaminoethoxy)phenphenyloxy]-10-nonadecene, hydroxy inner salt Following the procedure of Example 1 oleylaldehyde (15.99 g) was reacted with potassium t-butoxide in anhydrous t-butyl methyl ether and sec.-butyl lithium (1.4M in cyclohexane) plus anhydrous LiBr (2.0M in THF). Chromatography of the reaction product over silica using 5:1 cyclohexane/ether as the eluant yielded 11.58 g of (Z)-($\pm$)-1-t-butoxy-10-nonadecen-2-ol having the following characteristics.

NMR(CDCl$_3$) $\delta$ at 2.0 (m, 4, CH$_2$—CH=CH), 2.5 (m, 1, OH), 3.0–3.8 (m, 3H), 5.3 (m, 4, vinyl H). Analysis: Calc'd. for C$_{22}$H$_{44}$O: C, 81.41; H, 13.66; Found: C, 81.22; H, 13.93.

The above compound was reacted with ethyliodide via a Williamson synthesis according to the procedure of Example 1 to form an ethyl ether on the hydroxy at C-2 and then the hydroxy at C-1 was deprotected (removal of t-butyl ether group with Lewis acid -FeCl$_3$ in Ac$_2$O) to yield, after hydrolysis of the acetate, (Z)-($\pm$)-2-ethoxy-10-nonadecen-1-ol having the following characteristics.

$R_f$=0.2 (2:1 cyclohexane/Ether).

NMR (CDCl$_3$) $\delta$ at 2.0 (m, 5, CH$_2$CH=CH—CH$_2$ and OH), 3.2–3.8 (m, 5, CH$_2$OCH(R)CH$_2$O), 5.4 (m, 2, CH=CH). Mass Spectrum: peaks at 326, 295.

The above compound was then converted by the procedure of Example 1 to (Z)-($\pm$)-2-ethoxy-1-[(2-trimethylaminoethoxy)phosphinyloxy]-10-nonadecene, hydroxy inner salt, having the following characteristics.

$R_f$=0.28 (10:5:1) chloroform/methanol/ammonium hydroxide).

NMR (CDCl$_3$) $\delta$ at 2.0 (m, 4, CH$_2$CH=CH—CH$_2$), 3.35 [s, 9, N$^+$(CH$_3$)$_3$], 4.3 (m, 2, POCH$_2$), 5.3 (m, 2, CH=CH);

Mass spectrum: peaks at 492, 184,86.

Molecular Wt. Calc'd. for C$_{26}$H$_{55}$NO$_5$P: 492.3818 Found: 492.3786.

EXAMPLE 3

Preparation of (Z,Z)-($\pm$)-2-Methoxy-1-[(2-trimethylaminoethoxy)phosphinyloxy]-10,13-nonadecadiene, hydroxy inner salt (Z,Z)-($\pm$)-1-t-butoxy-10,13-nonadecadiene-2-ol, from Example 1, was reacted with methyl iodide under Williamson conditions as in Example 1 to yield the mixed ether (Z,Z)-($\pm$)-1-t-butoxy-2-methoxy-10,13-nonadecadiene; and the ether on the C-1 hydroxyl was cleaved by ferric chloride in acetic anhydride to yield (Z,Z)-($\pm$)-2-methoxy-10,13-nonadecadien-1-ol having the following characteristics.

$R_f$=0.16 (2:1 cyclohexane/ether)

NMR (CDCl$_3$) $\delta$ at 2.1 (m, 5, 2CH$_2$—CH$_2$—CH=CH and OH), 2.8 (m, 2, CH=CH—CH$_2$—CH=CH), 3.45 (s, 3, OCH$_3$), 3.5 (brd s, 3H), 5.4 (m, 4, 2CH=CH).

Mass spectrum: peak at 310.

Following the procedure of Example 1, the above alcohol was transformed to the phosphoryl choline derivative, (Z,Z)-($\pm$)-2-methoxy-1-[(2-trimethylaminoethoxy)phosphinyloxy]-10,13-nonadecadiene, hydroxy inner salt, having the following characteristics.

$R_f$=0.2 (10:5:1 chloroform/methanol/ammonium hydroxide).

NMR (CDCl$_3$) $\delta$ at 2.0 (m, 4, 2 CH$_2$CH$_2$CH=CH), 2.7 (m, 2, CH=CH—CH$_2$—CH=CH), 3.3 (s, 12, N$^+$(CH$_3$)$_3$ and OCH$_3$), 3.8 (m, 4), 4.3 (m, 2, POCH$_2$), 5.3 (m, 4, 2CH=CH). Mass Spectrum: peaks at 476,184.

Molecular Wt. Calc'd. for C$_{25}$H$_{53}$NO$_5$P: 476.3505, Found: 476.3465.

Unsaturated aldehydes used as starting materials in the above and similar syntheses are either available commercially or are prepared for the corresponding alcohol-see J.O.C, 43, 2480 (1978).

The compounds of this invention inhibit PAF (10$^{-7}$ molar) induced human platelet aggregation at concentrations in the range 50–100 micromolar, but are aggregation inducers at higher concentrations. The compounds also induce aggregation in the absence of PAF, in similar experiments. Human platelet aggregation experiments were performed using the method of Born (Nature, 194, 927 (1962)). Citrated platelet-rich plasma (2.5–4.0 $\times 10^5$ platelets/ml) was used, and platelet aggregation was monitored at 37° C. with a Payton Aggregometer by the conventional optical density method. Platelets were treated with drug 2 minutes prior to addition of PAF, and optical density was measured 4 min later.

The compounds also inhibit the growth of tumor cells in vitro and in vivo. Their in vitro cytostatic activity was demonstrated by their ability to inhibit the growth of human leukemic cells (CCRF-CEM cell line). Table 1 below gives the results of such testing of several compounds representative of those in Formula I. In the Table, column 1 gives the name of the compound and column 2 the IC$_{50}$ (concentration giving 50% growth inhibition) in mcg/ml.

TABLE 1

| Compound Name | CCRF-CEM Cytotoxicity Screen IC$_{50}$ mcg/ml |
|---|---|
| (Z,Z)-($\pm$)-2-ethoxy-1-[(2-Trimethylaminoethoxy)phosphinyloxy]-10,13-nonadecadiene, hydroxy inner salt, | 6.0 |
| (Z)-($\pm$)-2-ethoxy-1-[(2-Trimethylaminoethoxy)phosphinyloxy]-10-nona- | 1.6 |

TABLE 1-continued

CCRF-CEM
Cytotoxicity Screen

| Compound Name | IC$_{50}$ mcg/ml |
|---|---|
| decene, hydroxy inner salt, (Z,Z)-(±)-2-methoxy-[(2-trimethylaminoethoxy)phosphinyloxy]-10,13-nonadecadiene, hydroxy inner salt, | 4.2 |

Their in vivo antineoplastic was demonstrated by their activity against X-5565 (multiple myeloma), a turmor maintained in C3H mice. The following protocol was employed. The tumor was removed from passage animals and minced into 1 to 3 mm square fragments using sterile techniques. Tumor pieces were checked for sterility using both Antibiotic Medium 1 and Brain Heart Infusion (Difco; Detroit, MI). Recipient mice were shaved and tumor pieces were implanted subcutaneously in the axillary region by trocar. Drug therapy on the appropriate schedule was initiated on the day after tumor implant. The compound was dissolved in saline for all experiments. All animals were weighed at the beginning and end of drug treatment. Food and water were provided ad libitum. Each test group contains 5 animals. On days 10 to 12, two dimensional measurements (width and length) of all tumors were taken using vernier calipers. Tumor weights were calculated from these measurements using the following formula:

*Tumor Weight (mg) = Tumor Length (mm) X Tumor Width (mm)$^2$/2*

For all data, the tumor weight was rounded to the nearest tenth of a gram for analysis. No group is included in the analysis for therapeutic activity in which deaths attributable to drug toxicity exceeded 30 percent of the treated group.

In Table 2 which follows, column 1 gives the name of the compound; column 2, the dose level; column 3, the percent inhibition of the tumor; and column 4, the toxic deaths. Drug and control dosages were administered I.P. daily for 10 days.

TABLE 3

Activity Against X-5563 (multiple myeloma)

| Compound Name | Dose Level mg/kg | Percent Inhibition of Tumor | Toxic Deaths |
|---|---|---|---|
| (Z)-(±)-2-ethoxy-1-[(2-trimethylaminoethoxy)phosphinyloxy]-10-nonadecene, hydroxy inner salt, | 50 | 47 | 1/10 |
| (Z,Z)-(±)-2-ethoxy-1-[(2-trimethylaminoethoxy)phosphinyloxy]-10,13-nonadecadiene, hydroxy inner salt | 70 | 31 | 2/10 |

We claim:

1. A compound of the formula

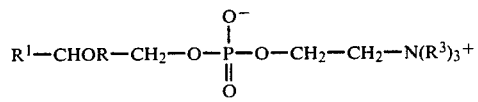

wherein R is $C_{1-6}$ alkyl, $R^1$ is a straight chain $C_{10-24}$ hydrocarbon radical containing at least one ethyleneic or acetylenic unsaturation; and each $R^3$ is individually methyl or ethyl.

2. A compound according to claim 1 in which $R^3$ is methyl.

3. A compound according to claim 1 in which R is ethyl or methyl.

4. A compound according to claim 1 in which $R^1$ is a $C_{12-24}$ unsaturated hydrocarbon radical containing at least one ethylene or acetylene group.

5. A compound according to claim 4 in which the unsaturated hydrocarbon group has 17 carbon atoms.

6. A compound according to claim 1 in which all $R^3$'s are methyl.

7. A compound according to claim 1, said compound being (Z,Z)-(±)-2-ethoxy-1-[(2-trimethylaminoethoxy)phosphinyloxy]-10,13-nonadecadiene, hydroxy inner salt.

8. A compound according to claim 1, said compound being (Z,Z)-(±)-2-methoxy-1-[(2-trimethylaminoethoxy)phosphinyloxy]-10,13-nonadecadiene, hydroxy inner salt.

9. A compound according to claim 1, said compound being (Z)-(±)-2-ethoxy-1-[(2-trimethylaminoethoxy)phosphinyloxy]-10-nonadecene, hydroxy inner salt.

* * * * *